(12) United States Patent
Coleman

(10) Patent No.: US 6,655,204 B2
(45) Date of Patent: Dec. 2, 2003

(54) ELASTOMERIC MATERIAL THICKNESS TEST FIXTURE

(75) Inventor: James W. Coleman, North Scituate, RI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 32 days.

(21) Appl. No.: 10/043,043

(22) Filed: Jan. 9, 2002

(65) Prior Publication Data

US 2003/0126922 A1 Jul. 10, 2003

(51) Int. Cl.[7] .............................................. G01L 5/04
(52) U.S. Cl. ....................................................... 73/159
(58) Field of Search ........................................... 73/159

(56) References Cited

U.S. PATENT DOCUMENTS 6,095,000 A * 8/2000 Esclar et al. ................... 73/866

* cited by examiner

Primary Examiner—Edward Lefkowitz
Assistant Examiner—Jermaine Jenkins
(74) Attorney, Agent, or Firm—James M. Kasischke; Michael F. Oglo; Jean-Paul A. Nasser

(57) ABSTRACT

The present invention relates to an elastomeric material thickness test fixture. The test fixture comprises a cylinder having an interior space for receiving at least one sheet of a material to be tested, and a piston movable relative to the cylinder for applying a holding force to the at least one sheet. The piston has a through hole to allow a test medium to be used to study chemical attack to come into contact with the at least one sheet. A process for allowing assessment of chemical attack on thick elastomeric materials using the test fixture is also described.

10 Claims, 3 Drawing Sheets

ELASTOMERIC MATERIAL THICKNESS TEST FIXTURE

STATEMENT OF GOVERNMENT INTEREST

The invention described herein may be manufactured and used by or for the Government of the United States of America for governmental purposes without the payment of any royalties thereon or therefor.

CROSS-REFERENCE TO OTHER PATENT APPLICATIONS

Not applicable

BACKGROUND OF THE INVENTION (1) Field of the Invention

The present invention relates to a test fixture which allows the assessment of chemical attack on thick elastomeric materials without the introduction of differences due to sample preparation and to a process of using the test fixture.

(2) Description of Prior Art

Various devices have been used in the prior art for determining the properties of sheet materials. Some of these devices are illustrated in U.S. Pat. Nos. 4,406,743 to Gunderson, 4,552,042 to Barker et al., 5,311,767 to Mathews et al., 6,085,579 to Herrlein, and 6,095,000 to Esclar et al. The Gunderson patent discloses a method and apparatus for edgewise compression testing of flat sheets. The Barker et al. and Mathews et al. patents each disclose the clamping of an elastomeric sheet to be tested between two dies. The Herelein patent discloses a method for assessing absorbent structures which utilizes a fluid filled cylinder disposed on top of the structure to be evaluated. The Esclar et al. patent describes a method and apparatus for feeding a treatment liquid to a sample.

The assessment of chemical attack on thick section elastomeric materials has been difficult to perform due to the need to extract small samples from the thick section for testing. Often, methods used to remove samples for testing, directly affect the results of the material tests due to the introduction of small surface defects such as machining marks, heat which changes the cure of the material, and swell introduced during water jet cutting.

Thus, there remains a need for a non-intrusive test for sheets of elastomeric materials.

SUMMARY OF THE INVENTION

Accordingly, it is an object of the present invention to provide a test fixture which allows the assessment of chemical attack on thick materials without the introduction of differences due to sample preparation.

It is a further object of the present invention to provide a test fixture as above which allows the assessment of chemical attack on thick elastomeric materials.

It is yet a further object of the present invention to provide a process for allowing the assessment of chemical attack on thick materials.

The foregoing objects are attained by the test fixture and the process of the present invention.

In accordance with the present invention, a test fixture is provided which broadly comprises a cylinder having an interior space for receiving at least one sheet of material, such as a sheet of elastomeric material, to be tested, and a piston movable relative to the cylinder for applying a holding force to the at least one sheet. The piston has a through hole for allowing a test medium to come into contact with the at least one sheet.

In accordance with the present invention, a process for allowing the assessment of chemical attack on thick elastomeric materials is provided. The process broadly comprises the steps of providing a cylinder having an interior space, positioning at least one sheet of elastomeric material within the interior space, placing a piston with a through hole into the cylinder to apply a holding force to apply a holding force to the at least one sheet, and immersing the cylinder with the at least one sheet and the piston into a test medium in which the chemical attack is to be assessed.

Other details of the test fixture and the process of the present invention, as well as other objects and advantages attendant thereto, are set forth in the following description and the accompanying drawings wherein like reference numerals depict like elements.

DESCRIPTION OF THE PREFERRED EMBODIMENT(S)

Figure 1:
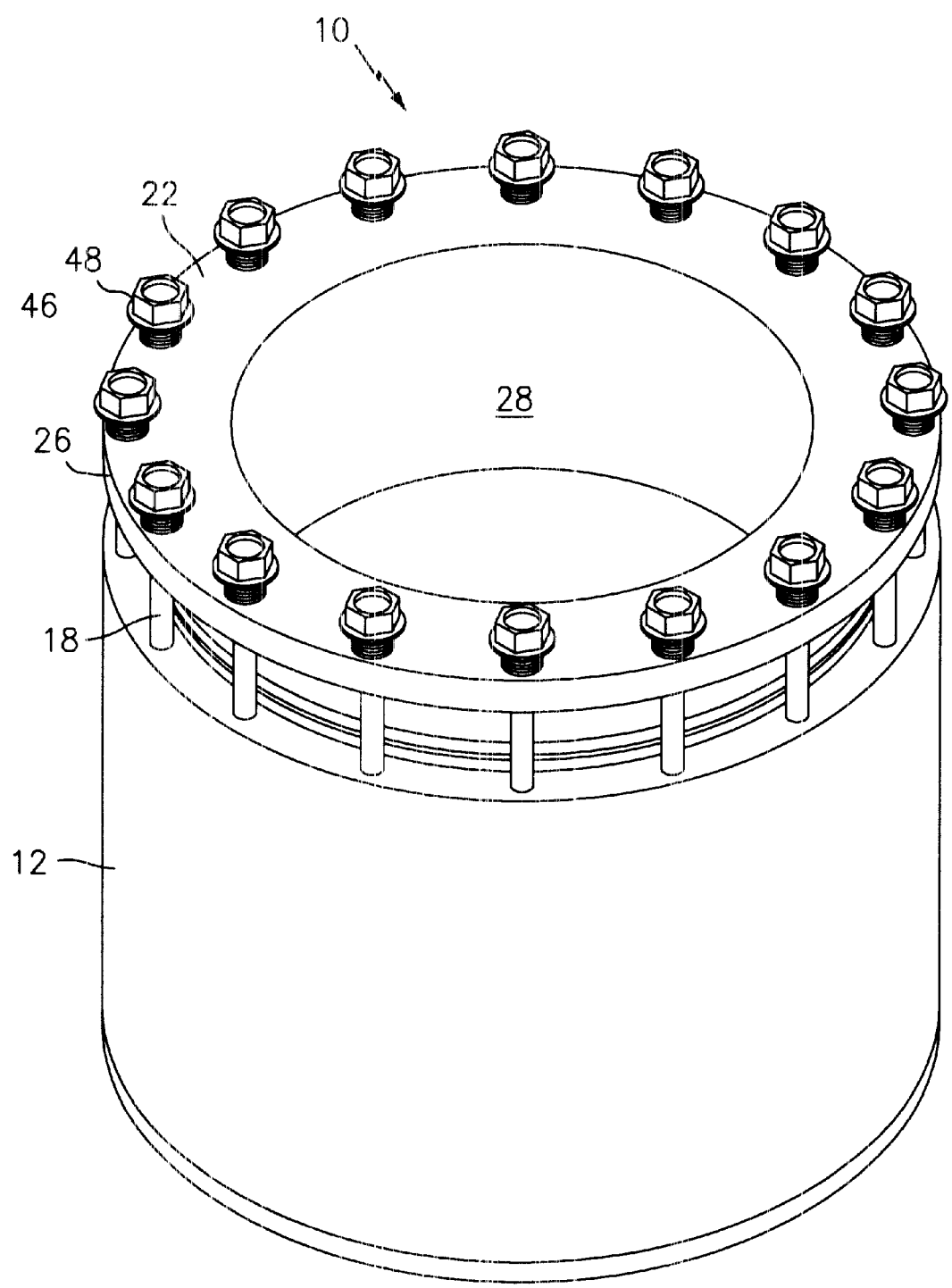
FIG. 1 is an isometric view of a test fixture in accordance with the present invention.

Referring now to the drawings, there is shown a test fixture 10 in accordance with the present invention. A cylinder 12 is provided having a cylindrical wall 14 and a bottom wall 16. Threaded studs 18 extend parallel with cylinder axis 20 from the top surface of cylindrical wall 14.

Figure 2:
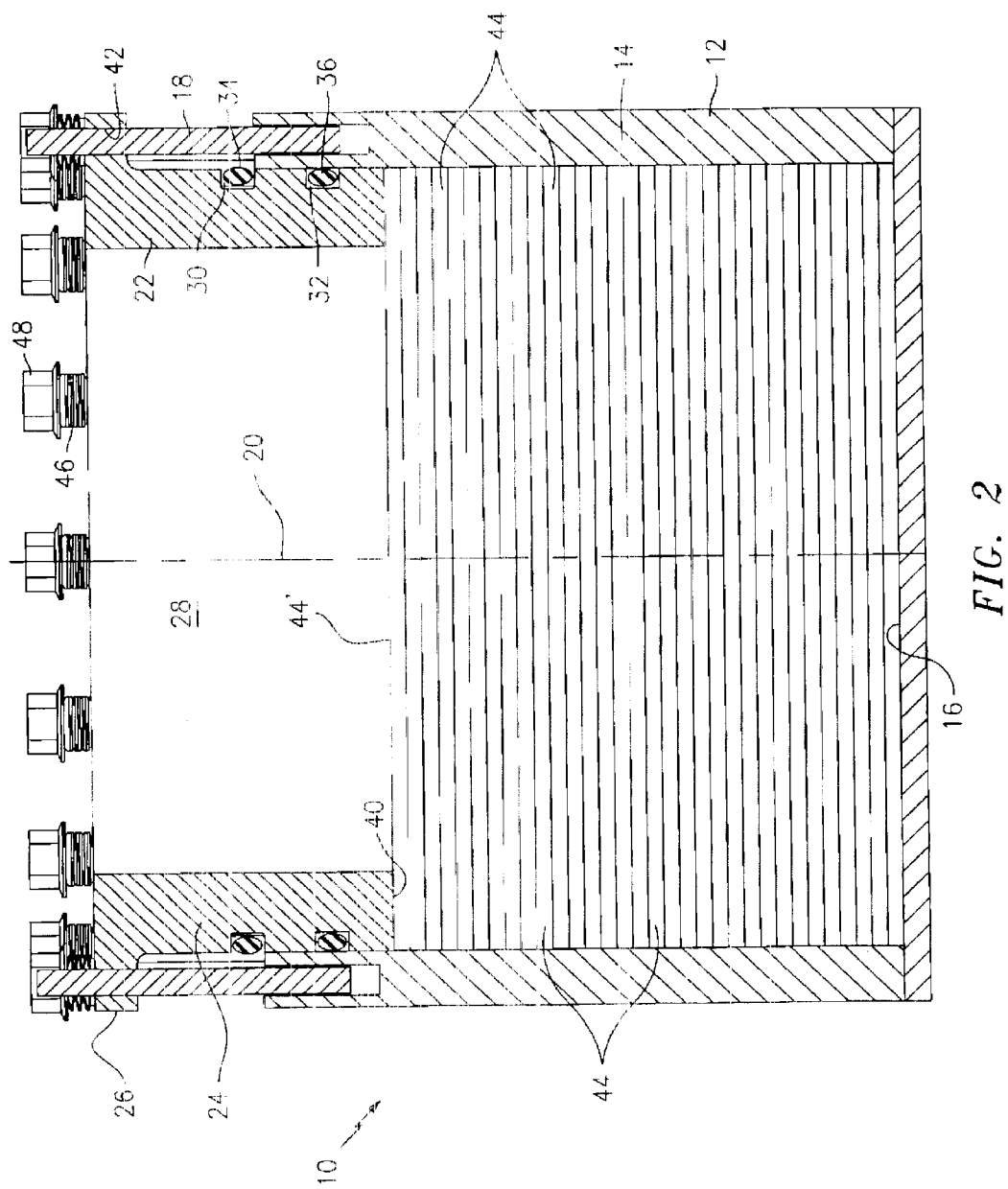
FIG. 2 is a sectional view of the test fixture of FIG. 1.
Figure 3:
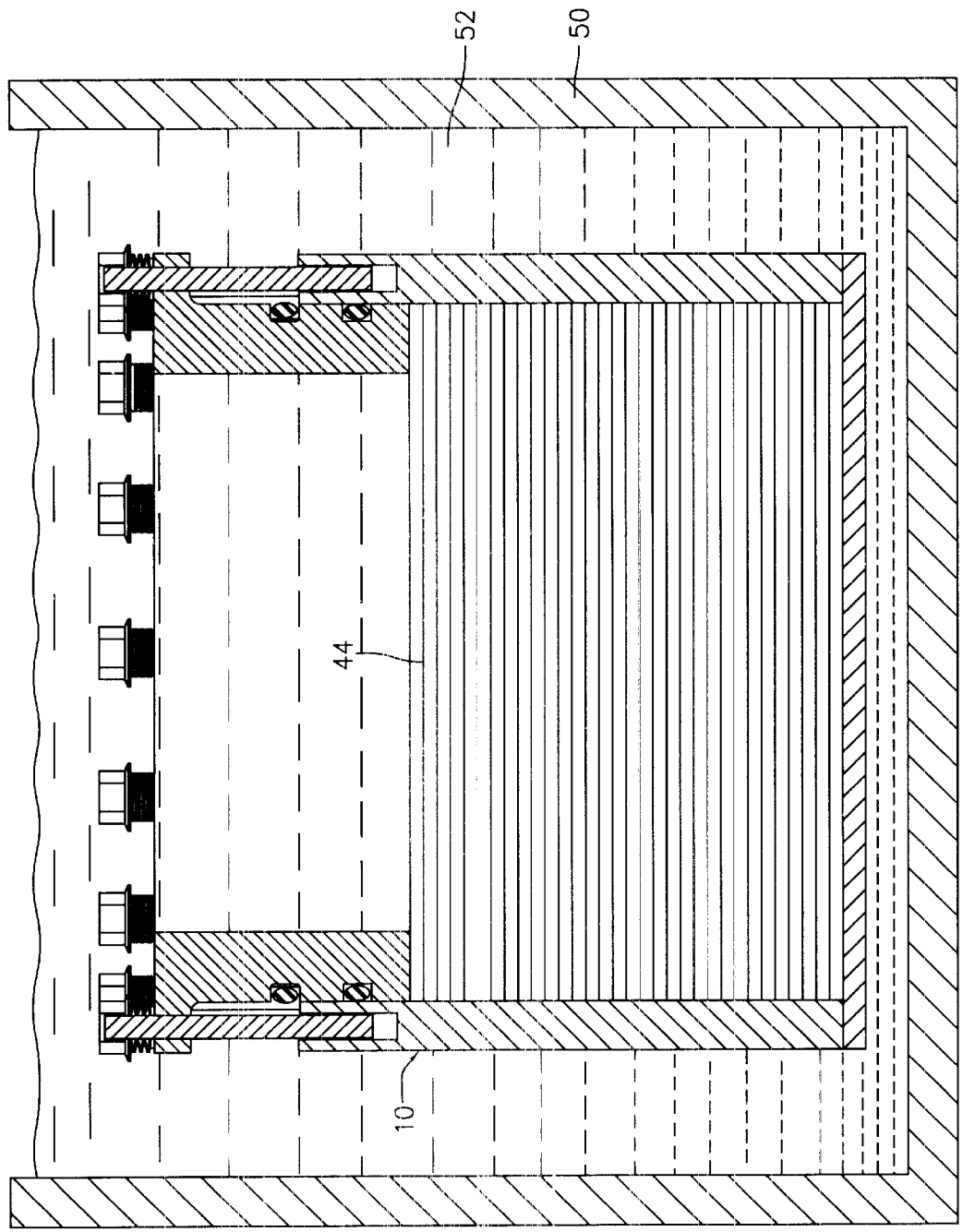
FIG. 3 illustrates the test fixture of the present invention immersed within a test medium.

Piston 22 has a body portion 24 and a flange portion 26 at one end. The central area defined inside body portion 24 is identified as central through hole 28. Body portion 24 has an outer diameter providing a sliding fit within cylinder 12. As can be seen from FIG. 2, the piston body portion 24 has first and second external annular grooves 30 and 32 formed thereon. First and second O-rings 34 and 36 are positioned in the annular grooves 30 and 32 providing sealing between piston 22 and cylinder 12. One end of body portion 24 terminates in a lip 40. Flange portion 26 has a larger outer diameter than body portion 24 and is positioned at the end of body portion 24 opposite lip 40. A plurality of apertures 42 corresponding with threaded studs 18 are formed in flange portion 26 and extend therethrough.

Upon assembly, test material sheets 44, such as rubber sheets or some other elastomeric material, are stacked within cylinder 12 inner wall 14 against bottom wall 16. With the appropriate number of sheets 44 in place, piston 22 is inserted into cylinder 12 with lip 40 positioned against a top layer 441 of test material sheets 44. Studs 18 are received in apertures 42. A spring member such as a Belleville washer 46 is positioned over each stud 24, and a nut such as hex nut 48 is threaded on each stud 24. When tightened, each hex nut 48 compresses its associated washer 46 which applies a force to piston 22 compressing sheets 44 between lip 40 and bottom wall 16. Each Belleville washer 46 further applies a force to the piston 22 which ensures that the piston 22 always applies a holding force to the sheets 44.

The Belleville washers 46 on studs 18 are used to ensure that there is sufficient force between the piston lip 40 and the elastomeric material sheets 44 while the elastomeric material sheets begin to take a permanent set under load. This prevents leakage into the assembly between lip 40 and top sheet 44'.

Once the test fixture 10 has been assembled, it is placed into a tank 50 containing a test medium 52, such as water, oil, air, etc., in which chemical attack will be assessed. Due to the construction of the fixture 10, all of the chemical attack acts on the material exposed through the hole 28 located in piston 22. The O-rings 34 and 36 and the seal between the piston lip 40 and the top layer 44' of material prevent any intrusion of the test medium 52 into the individual sheets 44. The actual test can be either performed under the normal operating conditions being assessed or under accelerated conditions by increasing the temperature of the test medium.

Upon completion of the intended exposure, the test fixture 10 is removed from the test medium 52 and the tank 50 and disassembled. Each individual elastomeric material sheet 44 provides an adequate amount of material to statistically assess the effect of the chemical attack by cold stamping tensile test specimens for tensile tests. By recording the testing results as a function of the depth into the assembly, the effect of thickness can be assessed. The first layer 44' represents the surface of the thick elastomeric material section, while each successive layer represents the results deeper into the thick section.

Different layer thicknesses can be used to change the resolution of depth on the assessment of chemical attack as a function of depth or thickness. Varying layer thickness assemblies can be used to assess the accuracy of the test results for the same depth.

The test fixture of the present invention allows for testing of the effect of chemical attack on thick section elastomers without the introduction of differences used by sample preparation. Using existing methods for sample preparation such as band saw cutting and water jet cutting often introduce flaws into the sample surface and can change the chemical composition of the material being tested by adding heat or water to the sample. The present invention eliminates the need to prepare the samples for testing using these intrusive sample preparation methods.

The test fixture of the present invention can be designed to accommodate a variety of overall thicknesses assessed by changing the height of the cylinder 12 and the height of the piston 22. Chemical attack can also be imposed on both sides of the sample, by using an open-ended cylinder with adequate sealing geometry in lieu of the cylinder 12.

While the test fixture of the present invention has been described as being used in the testing of elastomeric sheet materials, it could also be used to assess chemical attack on non-elastomeric sheet materials.

While the test fixture has been described as containing a plurality of sheets to be tested, it should be recognized that IT the test fixture would work equally well if only one sheet of material to be tested was placed in the cylinder.

While the piston has been described as having a central through hole to allow a test medium to come into contact with the material being tested, the central through hole could be replaced by a plurality of through holes if desired.

While the test fixture uses bolting hardware to join the piston to the cylinder, other types of hardware could be used to join the cylinder to the piston if desired.

It is apparent that there has been provided in accordance with the present invention an elastomeric material thickness test fixture which fully satisfies the objects, means and advantages set forth hereinbefore. While the invention has been described in the context of specific embodiments thereof, other alternatives, modifications, and variations will become apparent to those skilled in the art having read the foregoing description. Accordingly, it is intended to embrace those alternatives, modifications, and variations as fall within the broad scope of the appended claims.

What is claimed is:

1. A test fixture for testing sheets of material comprising:
   a cylinder having a side wall and a bottom surface defining an interior space for receiving at least one sheet of material to be tested;
   a piston slidable within said cylinder, said piston and said cylinder bottom surface cooperating for applying a holding force to said at least one sheet, said piston having a through hole for allowing a test medium to come into contact with said at least one sheet; and
   means for applying force joined between said piston and said cylinder for applying a force to said piston and causing said piston maintain a position within said cylinder and into a position where said piston contacts a surface of said at least one sheet.

2. The test fixture according to claim 1 wherein said force applying means comprises:
   a plurality of threaded studs connected to said cylinder at said cylinder side wall, said piston having a flange with a plurality of apertures therethrough corresponding to said plurality of studs for receiving said studs;
   a spring means positionable on each said stud received in one said piston flange aperture; and
   a nut threadable on each said stud, said nut compressing said spring means, and said spring means exerting force on said piston flange for ensuring that said piston remains in contact with said surface of said at least one sheet.

3. The test fixture according to claim 2 wherein said spring means comprises a Belleville washer.

4. The test fixture according to claim 1 wherein:
   said piston has at least one annular groove formed on an exterior surface thereof; and
   said test fixture further comprising a seal means positioned within said at least one annular groove for preventing leakage between said piston and said cylinder.

5. The test fixture according to claim 4 wherein:
   said piston has two spaced apart annular grooves; and
   said seal means comprises an O-ring seated within each of said annular grooves.

6. A test fixture for testing sheets of material comprising:
   a cylinder having a side wall and a bottom surface defining an interior space for receiving at least one sheet of material to be tested;
   a piston having a flange positioned exterior of said cylinder and a body portion slidable within said cylinder, said flange and body portion defining a through hole inside said piston, and said piston body portion and said cylinder bottom surface cooperating for retaining said at least one sheet therebetween;
   a sealing means positioned between said cylinder side wall and said piston body portion; and
   a fastening means joined between said piston flange and said cylinder side wall for retaining said piston within said cylinder.

7. The test fixture according to claim 6 wherein said fastening means comprises:
   a plurality of threaded studs connected to said cylinder at said cylinder side wall, said piston flange having a plurality of apertures therethrough corresponding to said plurality of studs for receiving said studs;

a spring means positionable on each said stud received in one said piston flange aperture; and a nut threadable on each said stud, said nut compressing said spring means, and said spring means exerting force on said piston flange for ensuring that said piston remains in contact with said surface of said at least one sheet.

8. A process for allowing the assessment of chemical attack on thick elastomeric materials comprising:

providing a cylinder having an interior space;

positioning at least one sheet of elastomeric material within said interior space;

fastening a piston with a through hole within said cylinder for retaining said at least one sheet of elastomeric material within said interior space; and immersing said cylinder with said at least one sheet and said piston into a test medium in which said chemical attack will be assessed.

9. The process according to claim 8 wherein said positioning step comprises positioning a stack of elastomeric sheets within said interior space.

10. The process according to claim 8 further comprising:

removing said cylinder and said fastened piston from said test medium;

removing said piston from said cylinder;

removing said at least one sheet from said interior space; and measuring physical properties of each said at least one sheet.

* * * * *